United States Patent
Bengtsson et al.

(10) Patent No.: US 9,636,461 B2
(45) Date of Patent: May 2, 2017

(54) SYSTEM FOR OPTIMIZING A DRUG DOSAGE REGIMEN OVER TIME

(75) Inventors: Henrik Bengtsson, Taastrup (DK); Toke Folke Christensen, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 81 days.

(21) Appl. No.: 14/115,799

(22) PCT Filed: May 2, 2012

(86) PCT No.: PCT/EP2012/058035
§ 371 (c)(1),
(2), (4) Date: Feb. 19, 2014

(87) PCT Pub. No.: WO2012/152628
PCT Pub. Date: Nov. 15, 2012

(65) Prior Publication Data
US 2014/0200545 A1  Jul. 17, 2014

Related U.S. Application Data (60) Provisional application No. 61/485,291, filed on May 12, 2011.

(30) Foreign Application Priority Data

May 6, 2011  (EP) ..................................... 11165063

(51) Int. Cl.
*A61M 5/24* (2006.01)
*G06F 19/00* (2011.01)
(Continued)

(52) U.S. Cl.
CPC ........... *A61M 5/24* (2013.01); *A61B 5/14532* (2013.01); *A61M 5/3157* (2013.01);
(Continued)

(58) Field of Classification Search
CPC ........ A61M 5/1723; A61M 2005/1726; A61M 2230/201; A61M 5/14244;
(Continued)

(56) References Cited

U.S. PATENT DOCUMENTS

| 4,731,726 A | 3/1988 | Allen, III |
| 6,192,891 B1 * | 2/2001 | Gravel et al. ................. 604/187 |

(Continued)

FOREIGN PATENT DOCUMENTS

| CN | 101125086 A | 2/2008 |
| EP | 1048310 A2 | 11/2000 |

(Continued)

OTHER PUBLICATIONS

Blonde, L. et al., Patient-Directed Tritation for Achieving Glycaemic Goals Using a Once-Daily Basal Analogue: An Assessment of Two Different Fasting Plasma Glucose Targets, Daibetes, Obesity and Metabolism, vol. 11, 2009, pp. 623-631.

*Primary Examiner* — Imani Hayman
*Assistant Examiner* — Hamza Darb
(74) *Attorney, Agent, or Firm* — Leon Y. Lum (57) ABSTRACT

A system for optimizing a patient's basal insulin dosage regimen over time, adapted to determine from blood glucose values whether and by how much to vary a patient's present recommended amount of the insulin-containing drug in order to maintain the patient's future blood glucose level measurements within a predefined range, and wherein a given blood glucose value is disregarded if no patient-actuated operation being indicative of the administration of a dose of an insulin containing drug has been detected in a pre-defined amount of time prior to the determination of the given blood glucose value.

10 Claims, 7 Drawing Sheets

(51) Int. Cl.
*A61B 5/145* (2006.01)
*A61M 5/315* (2006.01)
*A61M 5/32* (2006.01)
*G06Q 50/22* (2012.01)
*A61M 5/31* (2006.01)

(52) U.S. Cl.
CPC ...... *A61M 5/31568* (2013.01); *A61M 5/3202* (2013.01); *G06F 19/3406* (2013.01); *G06F 19/3456* (2013.01); *G06F 19/3468* (2013.01); *G06Q 50/22* (2013.01); *A61M 2005/3125* (2013.01); *A61M 2005/3126* (2013.01); *A61M 2205/50* (2013.01); *A61M 2205/8206* (2013.01)

(58) Field of Classification Search
CPC ...... A61M 2005/3126; A61M 2205/50; A61M 2205/8206; A61B 5/14532; A61B 5/4839; A61B 5/14865
USPC ............. 604/890.1–892.1, 504, 66–67
See application file for complete search history.

(56) References Cited

U.S. PATENT DOCUMENTS

| | | |
|---|---|---|
| 7,491,187 B2 | 2/2009 | Van Den Berghe et al. |
| 2004/0135078 A1* | 7/2004 | Mandro et al. ......... 250/231.13 |
| 2005/0182358 A1* | 8/2005 | Veit et al. ................. 604/93.01 |
| 2005/0192494 A1* | 9/2005 | Ginsberg ..................... 600/365 |
| 2008/0288180 A1* | 11/2008 | Hayter et al. .................. 702/23 |
| 2009/0005726 A1 | 1/2009 | Jones et al. |
| 2009/0253970 A1 | 10/2009 | Bashan et al. |
| 2009/0253973 A1 | 10/2009 | Bashan et al. |
| 2010/0016700 A1 | 1/2010 | Sieh et al. |

FOREIGN PATENT DOCUMENTS

| | | |
|---|---|---|
| JP | 2006507856 A | 3/2006 |
| WO | 2005/046559 A2 | 5/2005 |
| WO | 2009/146119 A2 | 12/2009 |
| WO | 2010/098931 A1 | 9/2010 |

* cited by examiner

SYSTEM FOR OPTIMIZING A DRUG DOSAGE REGIMEN OVER TIME

CROSS-REFERENCE TO RELATED APPLICATIONS

This application is a 35 U.S.C. §371 National Stage application of International Application PCT/EP2012/058035 (WO2012/152628), filed May 2, 2012, which claimed priority of European Patent Application 11165063.6, filed May 6, 2011; this application claims priority under 35 U.S.C. §119 of U.S. Provisional Application 61/485,291; filed May 12, 2011.

The present invention generally relates to systems and methods allowing a patient to optimize a drug dosage regimen over time.

BACKGROUND OF THE INVENTION

In the disclosure of the present invention reference is mostly made to the treatment of diabetes by delivery of insulin, however, this is only an exemplary field of use for the present invention.

Type 2 diabetes is a progressive disease in which β-cell function deteriorates. Initiating therapy with oral agents is a reasonable approach to take with most patients, the exception being patients with extreme hyperglycemia (fasting plasma glucose >250 mg/dl). These patients require insulin to lower glucose levels. Otherwise, starting with oral therapy can be very effective, especially in patients with a short duration of diabetes and, thus, relatively adequate β-cell function. However, during the course of the decease many patients sooner or later will need therapy with insulin. When determining whether a patient should be put on insulin therapy, it is helpful to look to the guidelines for glycemic control. The American Diabetes Association (ADA) and American College of Endocrinology (ACE) publish goals for A1C, postprandial glucose, and fasting/pre-prandial glucose. Most patients who are unable to achieve these goals using oral agents are candidates for insulin therapy.

One type of initial insulin therapy for Type 2 diabetics is to use once-daily injections with a long-acting insulin such as Levemir® from Novo Nordisk, often in combination with oral antidiabetic agents. However, to be successful, insulin therapy requires timely and appropriate titration of dosages. For example, in combination with oral antidiabetic agents it is recommended to initiate Levemir® treatment with once daily administration at a dose of 10 U or 0.1-0.2 U/kg. The dose of Levemir® should then be titrated based on individual patients' needs, e.g. based on average (3-7 measurements) self-measured pre-breakfast blood glucose (BG) values. For example, for a calculated value of >10.0 mmol/L it is recommended to adjust the Levemir® dose with +8 units, for a calculated value of 9.1-10.0 mmol/L it is recommended to adjust the Levemir® dose with +6 units, for a calculated value of 8.1-9.0 mmol/L it is recommended to adjust the Levemir® dose with +4 units, for a calculated value of 7.1-8.0 mmol/L it is recommended to adjust the Levemir® dose with +2 units, and for a calculated value of 6.1-7.0 mmol/L it is recommended to adjust the Levemir® dose with +2 units. If one BG measurement is 3.1-4.0 mmol/L it is recommended to adjust the Levemir® dose with −2 units, and if one BG measurement is <3.1 mmol/L it is recommended to adjust the Levemir® dose with −4 units. The calculation of the average pre-breakfast BG values as well as the resulting Levemir® dose adjustments may either be performed by the patient him/herself or by a doctor/nurse based on BG values supplied by the patient. As appears, such a regimen is both time-consuming as well as prone to mistakes. This said, self-titration regimens are considered to facilitate empowerment of patients, allowing them to become more involved in their treatment which may then result in improved glycaemic control.

Correspondingly, devices and systems have been provided in which recommendations are generated based on self-measured BG values by a pre-programmed algorithm, e.g. corresponding to the relatively simple titration regimen described above. Indeed, much more sophisticated algorithms can be implemented taking into account e.g. patient characteristics and other variable inputs, see e.g. US 2009/0253970. The algorithm may be in the form of software adapted to run on different platforms, e.g. PC, PDA or smartphone, or it may be impeded in a device such as a blood glucose meter (BGM), see e.g. US 2010/0016700. WO 2010/098931 discloses a drug delivery pen provided with a processor and an accelerometer whereby use of the pen can be detected, the information being used to guide a patient to use the pen correctly. WO 2005/046559 discloses a system adapted to detect and store information relating to use of drug delivery pen.

Although such automatically generated recommendations may be of great help to both medical staff and patients, the recommendations may be wrong if they are based on incorrect assumptions, especially that the patient follows the regimen as prescribed.

Having regard to the above, it is an object of the present invention to provide systems and methods supporting cost-effective optimization and control of patient self-titration of a medical regimen.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a system for optimizing a patient's basal insulin dosage regimen over time is provided, comprising a blood glucose meter for receiving a patient blood sample and generating a blood glucose data set corresponding to a blood glucose value of the patient blood sample (e.g. BG value and time), detecting means for detecting when a patient-actuated operation is performed, the operation being indicative of the administration of a dose of an insulin containing drug, and memory means adapted to receive (a) blood glucose data sets corresponding to a plurality of blood glucose values as a function of time, (b) data representing detected patient-actuated operations as a function of time, and (c) data representing an initial insulin dosage regimen. The system further comprises a processor operatively connected to the memory means, the processor being programmed to determine from the blood glucose data sets determined at a plurality of times whether and by how much to vary a component in the patient's present insulin dosage regimen (i.e. to provide a recommendation) in order to maintain the patient's future blood-glucose-level measurements within a predefined range, and output means for communicating to the patient a component in the patient's insulin dosage regimen. In such a system a given blood glucose data set can then be disregarded by the processor if no patient-actuated operation has been detected in a pre-defined amount of time prior to the generation of the given data set. Additionally, a given blood glucose data set corresponding to a blood glucose value outside a predefined range or taken at a non-prescribed time may also result in the blood glucose data set being disregarded.

In an exemplary embodiment the system is in the form of a drug delivery assembly comprising a drug delivery device comprising a reservoir for a drug or means for receiving a reservoir, an outlet for the drug, a drug expelling mechanism for expelling drug from the reservoir and out through the outlet, and a cap device releasably mountable on the drug delivery device and adapted to cover the outlet in a mounted position. The cap device comprises the blood glucose meter, the memory means and the processor, the output means, and the detecting means, wherein the detection means is adapted to detect a cap-off event when the cap has been at least partially de-mounted from the drug delivery device for a predetermined amount of time, wherein a cap-off event is indicative of the administration of a dose of an insulin containing drug. In this way the recommendation can take into account that the patient has not used the drug delivery device in accordance with the regimen. For example, if the patient is supposed to take an amount of Levemir® at bed time, then failure to take off the cap e.g. in the time range 6:00-11:00 PM prior to determining a morning BG value (e.g. in the time range 6:00-9:00 AM) would result in the algorithm disregarding the BG value when calculating a recommendation. If the cap does not comprise a real time clock then a time range relative to BG measurement could be defined.

In an alternative embodiment the drug expelling mechanism can be set to expel a desired dose of drug when actuated, the drug delivery device comprising controller and memory means adapted to detect the size of an expelled dose and create a dose log representing detected dose sizes as a function of time, the expelling being indicative of the administration of a dose of an insulin containing drug. When such log data is transmitted to the cap device they can be used to effectively calculate recommendations. In a further alternative embodiment both the BGM and recommendation means are arranged in the drug delivery device per se.

In a further aspect a method for optimizing a patient's basal insulin dosage regimen over time is provided, comprising the steps of (i) determining a blood glucose value a plurality of times over time, (ii) detecting when a patient-actuated operation is performed, the operation being indicative of the administration of a dose of an insulin containing drug, and (iii) determining, based on determined blood glucose values, whether and by how much to vary a component in the patient's present insulin dosage regimen in order to maintain the patient's future blood-glucose-level measurements within a predefined range, wherein a given blood glucose value is disregarded if no patient-actuated operation has been detected in a pre-defined amount of time prior to the generation of the given blood glucose value. The term "glucose value" also covers an actual data set provided by a BGM sensor, i.e. before it is translated into an actual BG value. The method may be implemented by means of the above-disclosed systems.

The method may comprise the further step of providing an assembly comprising a blood glucose meter, a drug delivery device, and a processor configured to determine, based on blood glucose values, whether and by how much to vary a component in a patient's insulin dosage regimen in order to maintain the patient's future blood-glucose-level measurements within a predefined range. The patient-actuated operation may be expelling of a dose of drug from the drug delivery device. The drug delivery device may comprise a main part with a drug expelling mechanism and a cap adapted to be releasable mountable on the main part, the patient-actuated operation being the at least partial de-mounting of the cap from the drug delivery device for a pre-determined amount of time. The blood glucose meter may be arranged in the cap.

For further optimization and control of patient self-titration of a medical regimen, the invention provides in a further aspect a system for optimizing a patient's basal insulin dosage regimen over time, comprising a patient assembly and a display unit. The patient assembly comprises a blood glucose meter for determining a blood glucose value from a blood sample, first controller and memory means adapted to (i) store data representing an initial basal insulin dosage regimen, the dosage regimen comprising a recommended amount of an insulin-containing drug to be taken at recommended intervals, (ii) determine from blood glucose values determined at a plurality of times whether and by how much to vary the patient's present recommended amount of the insulin-containing drug in order to maintain the patient's future blood glucose level measurements within a predefined range, (iii) create a blood glucose value log representing blood glucose values as a function of time, and (iv) create a recommended amount log representing recommended amounts as a function of time, the patient further comprising means for transmitting log data to the display unit. The display unit comprises means for receiving log data from the drug delivery assembly, display means, and second controller and memory means adapted to (i) store the received log data, (ii) control the display means to at the same time display the blood glucose value log data and the recommended amount log data as a function of time. The patient assembly could be in the form of a BGM with imbedded software for making recommendations. The display unit could be in the form of a PC, e.g. for use by a medical practitioner, or a smart phone, e.g. for use by a patient. Communication between the two units could be wired or wireless. By showing recommendations and BG values at the same time the medical practitioner as well as the patient is given a tool which in a simple way acquires and presents data which may help in optimizing the patient's titration progress. The system may incorporate the above-described features for disregarding blood glucose data.

In an exemplary embodiment the patient assembly further comprises a drug delivery device comprising a drug reservoir or means for receiving a drug reservoir, an outlet for the drug, and an actuatable drug expelling mechanism for expelling drug from the reservoir and out through the outlet, as well as a cap releasably mountable on the drug delivery device and adapted to cover the outlet in a mounted position. In such an assembly the cap may comprise the blood glucose meter, the first controller and memory means, and the means for transmitting log data. In this way the patient is provided with a cap device which can be used as a simple add-on when adapted to be used with a specific type of drug delivery device, e.g. a traditional pen device.

The first controller and memory means may further be adapted to detect a cap-off event when the cap has been at least partially de-mounted from the drug delivery device for a pre-determined amount of time, and create a cap-off log representing detected cap-off events as a function of time. Correspondingly, the second controller and memory means of the display unit may be adapted to control the display means to additionally display the cap-off time log as a function of time. By providing the cap with means for detecting when the cap has been at least partly removed from the drug delivery device a very simple and cost-effective way of collecting and displaying information indicative of actual use of the drug delivery is provided, this supporting the medical practitioner when evaluating the patient's log data.

In a further exemplary embodiment the drug expelling mechanism can be set to expel a desired dose of drug when actuated, the first controller and memory means being further adapted to detect the size of an expelled dose and create a dose log representing detected dose sizes as a function of time. Correspondingly, the second controller and memory means may be adapted to control the display means to additionally display the dose log as a function of time. Drug delivery devices provided with electronic means for detecting the amount of actually expelled drug are known, see e.g. WO 08/037801. Such a device may be adapted to transmit data to a cap device, e.g. wirelessly, optically or via galvanic contacts.

In a further aspect of the invention an apparatus comprising a first member and a second member is provided, the first member comprising a receiving cavity in which at least a portion of the second member can be inserted in a first direction, and contact means adapted to engage the second member when inserted into the receiving cavity, the contact means being actuatable between an initial position and an actuated position, wherein the contact means is moved in a radial direction relative to the first direction when moved between the initial and actuated position. The cavity may have an oblong configuration defining a general axis, the first direction being generally parallel to the general axis.

In an exemplary embodiment the contact means comprises a moveable contact surface adapted to engage the second member when received in the receiving cavity, the contact surface being inclined relative to the general axis, this allowing an axial force exerted by the second member on the contact surface to move the contact surface in a radial direction. The contact surface may be arranged on a member, e.g. a spring member having a bias towards the initial position, which is either bendable or pivotable relative to the receiving cavity.

The first member may be a drug delivery device having a drug outlet, and the second member a cap adapted to cover the drug outlet when the drug delivery device is at least partly received in the receiving cavity of the cap, the cap comprising electronic detection means adapted to detect when the contact means is actuated, this being indicative of the drug delivery device being received in the cap. The electronic detection means may comprise a clock and a memory, the memory being adapted to store one or more time values corresponding to actuation of the contact means.

A display for a compact electronic device, e.g. a BGM cap device as described above, is often relatively small. Whether the device contains a rechargeable battery, a replaceable battery or a non-replaceable battery, there is a need for a battery indicator in order to show the remaining capacity of the battery. Normally the indicator is shown in all screen views, however, for a small display a relatively large part of the total area is normally reserved for the battery indicator at the expense of the primary information on the display.

Thus, in a further aspect of the invention an electronic device is provided comprising a processor, a display controllable by the processor, an energy source having a number of energy states, wherein the display comprises a main area controllable to indicate either a value for a given parameter (e.g. blood glucose level) or one of a number of energy states for the energy source, and wherein the main area of the display is controllable to be in a number of display states corresponding to a number of energy states. More specifically, in a first display state corresponding to a first energy state in which the energy level of the energy source is above or at a first limit, the display is controlled to show only a value for the given parameter, in a second display state corresponding to a second energy state in which the energy level of the energy source is below the first limit and above or at a second limit, the display is controlled to show both a value for the given parameter and an indication of the second energy state, and in a third display state corresponding to a third energy state in which the energy level of the energy source is below the second limit, the display is controlled to show only an indication of the third energy state.

In this way the user only has to think about recharge or battery change when it is necessary, and the entire area of a small display can be used for the at any time most relevant information.

In an exemplary embodiment, the display can be turned off and on whereby in the second state the display is controlled when turned on to first show an indication of the second energy state and after a given amount of time a value for the given parameter. When in the third state the display may be controlled when turned on to first show an indication of the third energy state and after a given amount of time to automatically turn off. In the second state the display may be controlled to shift (e.g. flash) between a value for the given parameter and an indication of the second energy state. In addition to the three states the display may have one or more intermediate states corresponding to energy states between the second and third energy states, wherein the display is controlled to show both a value for the given parameter and an indication corresponding to a given intermediate energy state, e.g. different flashing and/or change patterns.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of the exemplary embodiments reference will be made to the use of insulin.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
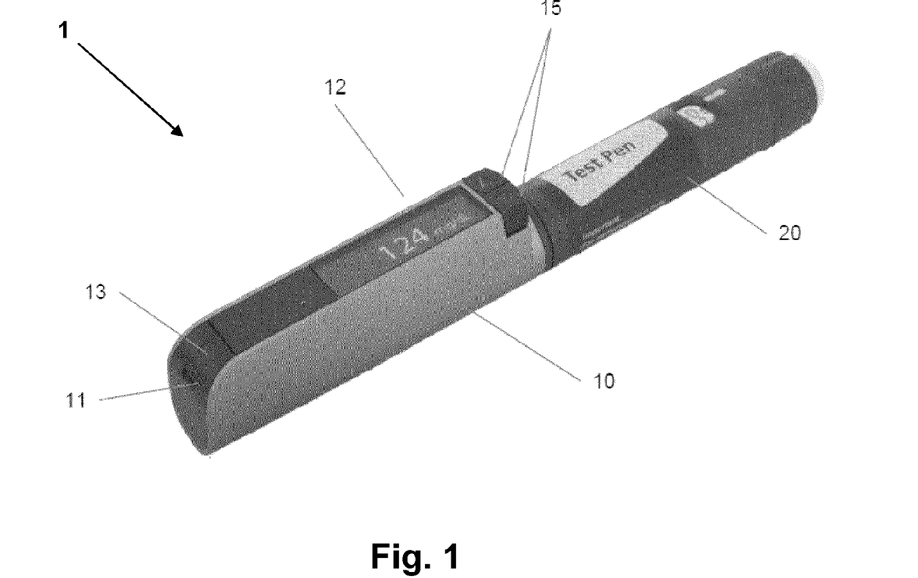
FIG. 1 shows a drug delivery device in combination with a mounted cap device.

FIG. 1 shows a drug delivery assembly 1 comprising a drug delivery device 20 containing an insulin formulation and onto which is mounted a cap device 10. The cap comprises a strip port for a BGM arranged in the interior of the cap, a display 12 adapted to show BG values as well as other values (e.g. a LCD or OLED), an input button 13 adapted to confirm a given value, e.g. a BG reading, as well as a set of up/down buttons 15 adapted to scroll in a given log, e.g. a BG log. The cap further comprises means for detecting when it has been removed from the drug delivery device as well as a port for uploading data to an external device (not shown).

The shown cap further comprises processor and memory means for calculating a recommended change in drug delivery. For example, if the cap was adapted to support a patient during initial titration in a once-daily injection regimen with a long-acting insulin such as Levemir® from Novo Nordisk in combination with oral anti-diabetic agents, then the cap device may be loaded with a simple algorithm corresponding the above-described titration guideline for Levemir®. For example, if the average of the 5 last BG measurements was 8.5 mmol/L the cap would recommend adjusting the Levemir® dose with +4 units. The recommendation could be prompted and displayed in several ways. For example, the user may have to prompt the device to display the recommendation by using the input button in a specified way. As the titration dose regimen is based on fasting BG and bed-time injection of insulin, removing the cap from the drug delivery device may also be used to prompt the cap. The recommendation could be shown as "+4 total 24 units" this indicating both the change in dosing and the total amount of insulin to inject.

Thus, in a situation of use, the delivery assembly 1 can be used to optimize a patient's basal insulin dosage regimen over time by (i) determining a blood glucose value a plurality of times over time, (ii) detecting when a patient-actuated operation is performed (here: removing the cap from the device), the operation being indicative of the administration of a dose of an insulin containing drug, and (iii) determining based on the blood glucose values whether and by how much to vary a component in the patient's present insulin dosage regimen in order to maintain the patient's future blood-glucose-level measurements within a predefined range, wherein a given blood glucose value is disregarded if no patient-actuated operation has been detected in a pre-defined amount of time prior to the generation of the given blood glucose value.

For example, if the patient is supposed to take an amount of Levemir® at bed time, then failure to take off the cap e.g. in the time range 6:00-11:00 PM prior to determining a morning BG (e.g. in the time range 6:00-9:00 AM) would result in the algorithm disregarding the BG value when calculating a recommendation. If the cap does not comprise a real time clock then a time range relative to BG measurement could be defined. Additionally, a given blood glucose data set corresponding to a blood glucose value outside a predefined range or taken at a non-prescribed time may also result in the blood glucose data set being disregarded.

As the patient uses the cap device 10 logs are created storing logs of (accepted) BG values, dose size recommendations as well as cap-off events. The log may be based on either real or relative time. In the latter case the relative time stamps would be provided with absolute time stamps when transferred to an external device.

Figure 2:
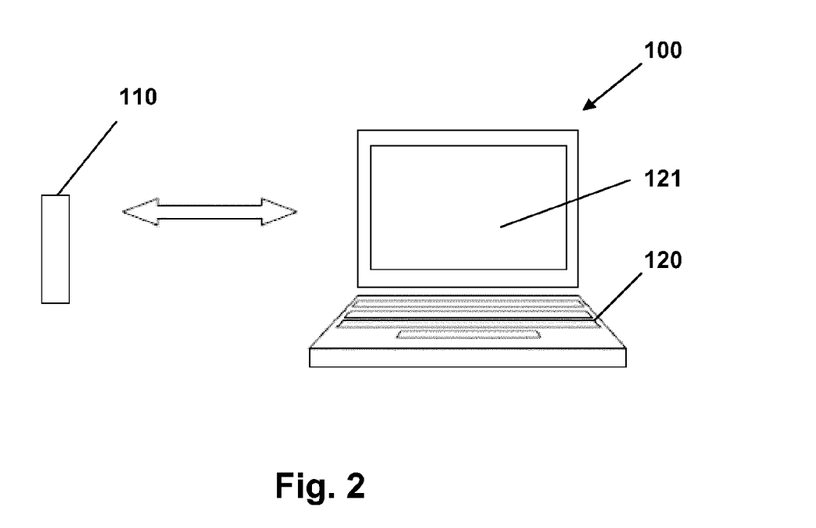
FIG. 2 shows a further cap device.

FIG. 2 shows a system 100 for optimizing a patient's basal insulin dosage regimen over time, and comprising a patient unit 110 and a display unit 120. The patient unit is in the form of a BGM cap device of the type shown in FIG. 1 and the display unit is in the form of a laptop computer. The shown units are adapted for wireless and bi-directional communication by e.g. RF such as Bluetooth, NFC or IR. Communication may be initiated by either device. Alternative communication may be by wire. When a patient is initiated on e.g. Levemir® patient specific parameters are uploaded to the cap device. Depending on how advanced the titration algorithm is more or less information will be needed, e.g. for a simple algorithm as described above the initial daily administration of a single dose of 10 U will be entered. As the patient uses the BGM cap BG values and recommended dose data will be logged in the memory for subsequent upload to the PC when the patient comes to visit the doctor's office.

Figure 3:
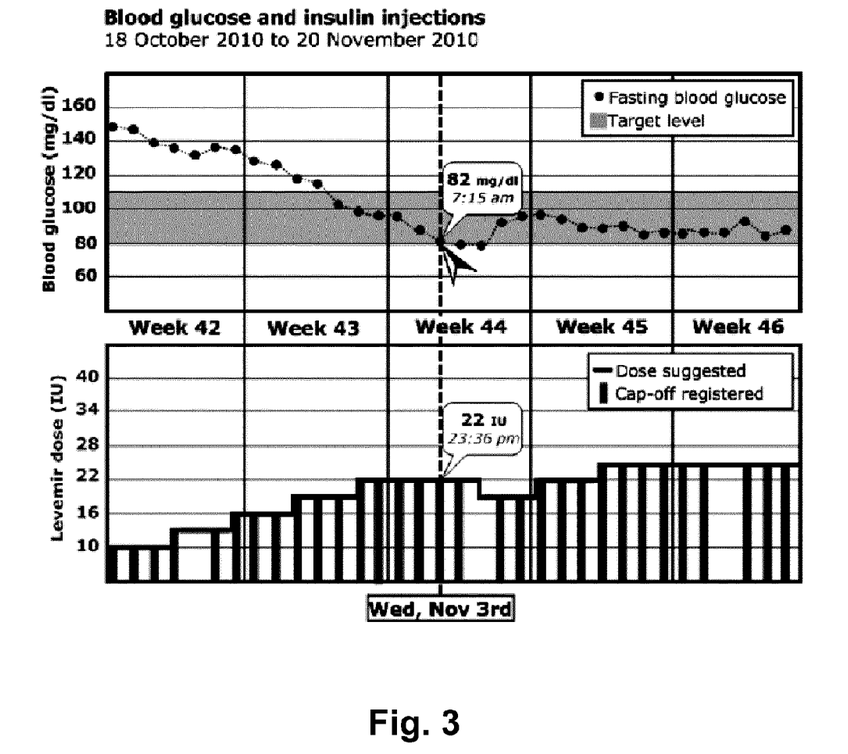
FIG. 3 shows a system for displaying information.

When the log data is uploaded to an external device such as a doctors' PC, the data may be displayed as shown in FIG. 3. As can be seen, the PC is provided with software presenting the BG values, recommendations and cap-off events as a function of time, each logged event being provided with an absolute time stamp. In this way a comprehensive overview is provided which can help the doctor evaluate the patient's titration regimen. The software is further adapted to provide statistic data and statistical analyses to further assist the doctor. Indeed, the same information could be uploaded to the patient's PC or to a smartphone.

Figure 4:
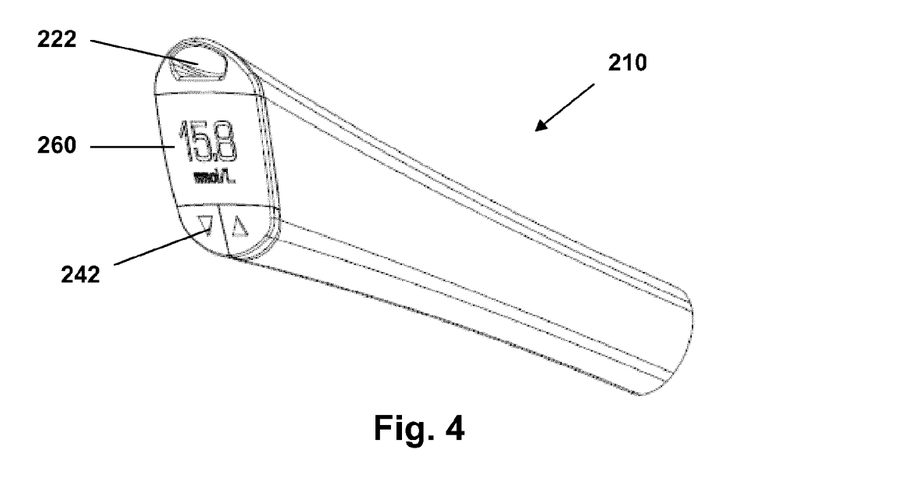
FIG. 4 shows graphs displaying patient information as a function of time.
Figure 5:
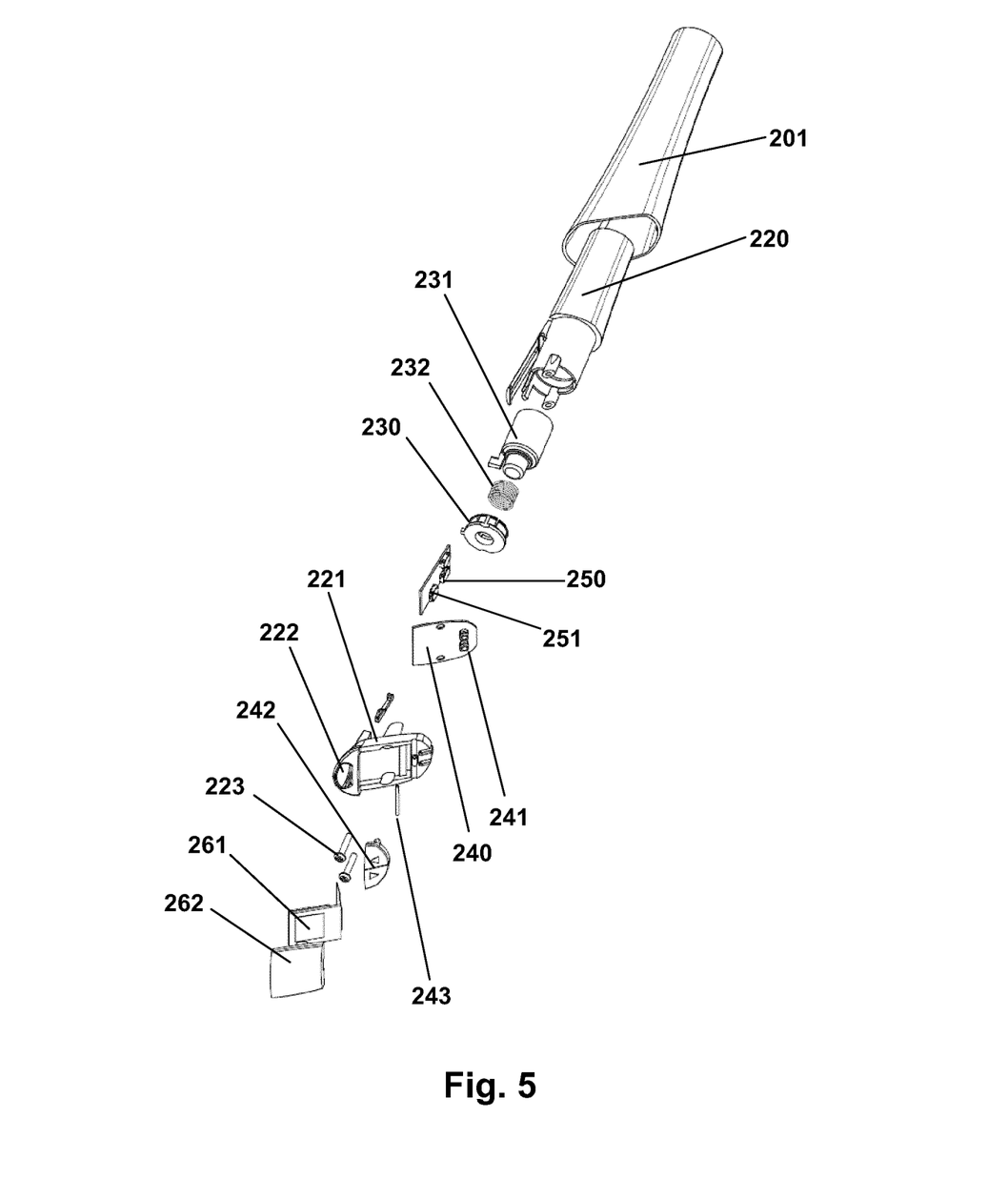
FIG. 5 shows an exploded view of the cap device of FIG. 2.

FIG. 4 shows an alternative configuration of a BGM cap 210 in which a strip port 222, a display 260 and user buttons 242 are arranged at the distal end of the cap. As seen in FIG. 5 the cap comprises a housing member 201 in which a generally tubular main chassis 220 is arranged, the latter having a top chassis 221 with a strip port 222 attached by screws 223. A spring support member 230 is attached to the main chassis. An actuator cup 231 is slidingly received in the main chassis in which it can travel between an un-loaded and a loaded position, the cup being biased towards its initial position by a spring 232 arranged between the spring support and the distal end of the cup, the cup being adapted to be moved distally when the cap is mounted on the distal end of a corresponding drug delivery device as seen in FIG. 1. The cap further comprises a first printed circuit board (PCB) 240 on which button switches 241 as well as an energy source and controller, memory and transmission means (not shown) are arranged, and a second PCB 250 on which cup-actuated switch means 251 and a BGM unit (not shown) are arranged. The switch means 251 is actuated when the cup 231 is moved axially thereby detecting a cap-off event. A display 261 is connected to the first PCB and covered by a transparent window member 262 attached to the top chassis to which further is attached two buttons 242 by means of an axle 243 allowing the buttons to pivot. The cap may further be provided with an accelerometer or an inertial sensor, this allowing the detected patient-actuated operation to be in the form of e.g. vertical position (indicative of air-shot) and shaking (indicative of mixing).

Figure 6:
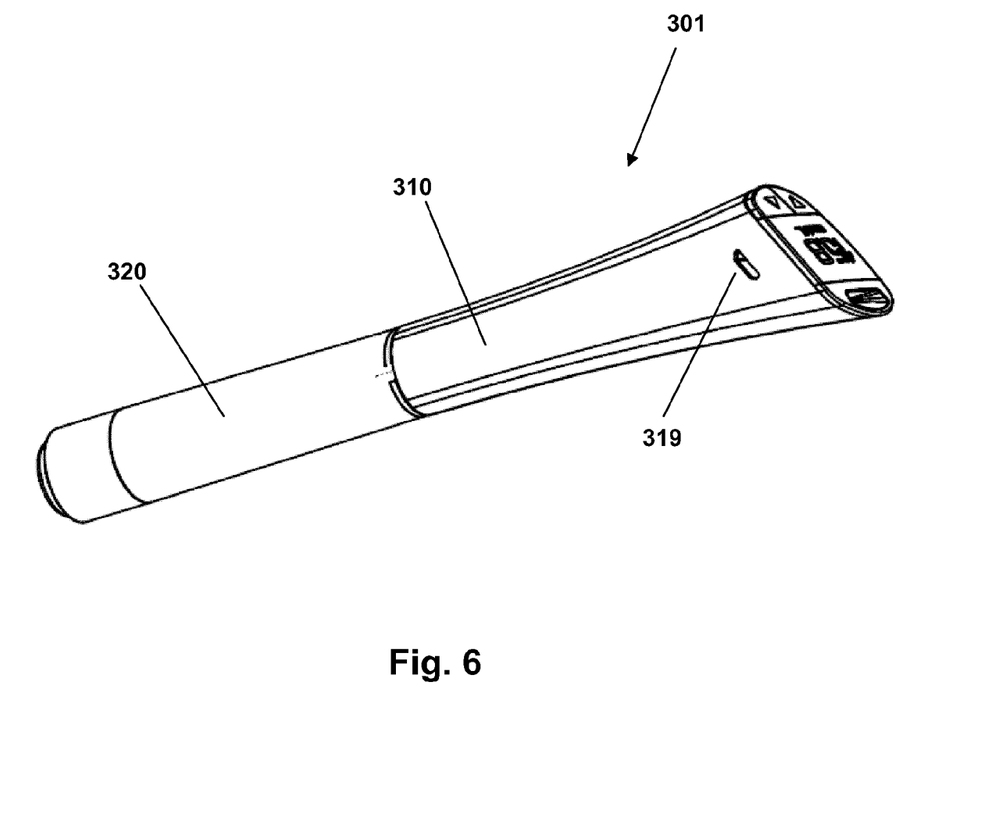
FIG. 6 shows a further cap device mounted on a drug delivery device.

FIG. 6 shows a drug delivery assembly 301 comprising a drug delivery device 320 of the type shown in FIG. 1 and onto which is mounted a cap device 310. The cap device is similar to the BGM cap device of FIG. 4, however, instead of wireless communication means the cap device is provided with an I/O port 319 adapted for wired communication.

In the shown embodiment of FIG. 1 the drug delivery device is a pre-filled pen device intended for single use only, however, the pen could also be a durable device intended to be used with exchangeable drug cartridges. In case the pen is of the durable type it may be provided with electronic means for detecting and creating a dose log which then could be transmitted to the cap device 10.

Figure 7:
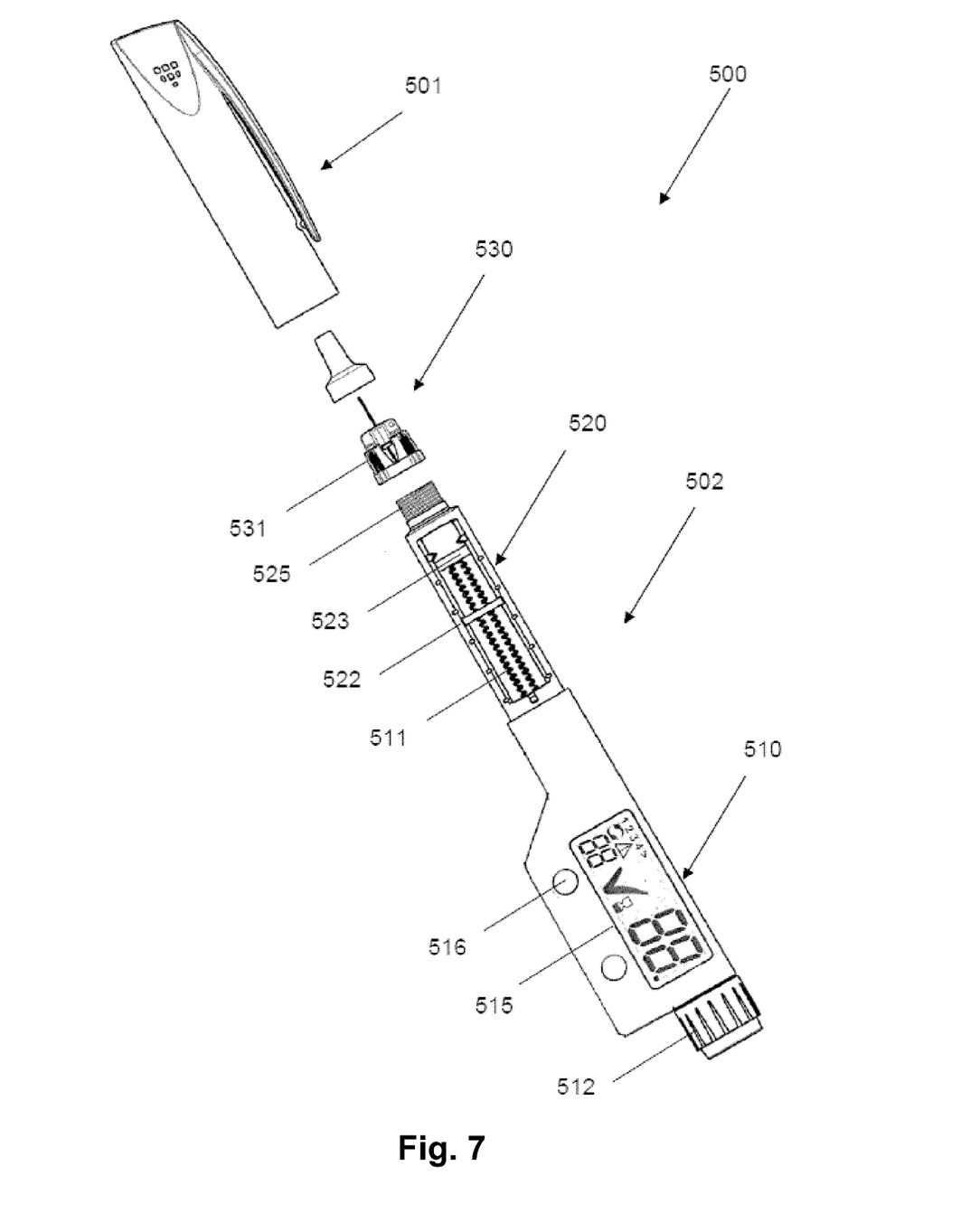
FIG. 7 shows a drug delivery means comprising electronic logging and display means.

FIG. 7 shows such a pen 500. The pen device comprises a cap portion 501 (here shown as a normal cap not related to the cap device 10) and a main portion 502 having a proximal part 510 in which a drug expelling mechanism is arranged, and a distal reservoir part 520 in which a replaceable drug-filled transparent cartridge 521 with a distal needle-penetratable septum is arranged and hold in place by a cartridge holder 522 releasably mounted to the proximal part, the cartridge holder having openings allowing a portion of the cartridge to be inspected. The cartridge is provided with a piston 523 driven by a piston rod 511 forming part of the expelling mechanism, the piston rod being adapted to be pushed back when a new cartridge is mounted. A proximal-most button 512 serves to manually set and expel a desired dose of drug. This type of a mechanical pen-formed drug delivery device is well known, see e.g. WO 99/38554 to which reference is made for further details in respect of the internal construction of the shown type of pen. The cartridge (or alternatively the cartridge holder) is provided with distal coupling means in the form of a hub mount 525 having, in the shown example, an external thread adapted to engage an inner thread of a hub 531 of a needle assembly 530. The proximal part further comprises a display 515, user actuatable keys 516 as well as electronic means (not shown) for detecting and storing information representing operations performed by the expelling mechanism. The detection means for detecting a set and/or expelled dose may be adapted to detect directly or indirectly the position of the piston rod, see e.g. U.S. Pat. No. 6,585,698 which is hereby incorporated by reference. The electronic means is adapted to store data representing injections performed by the user in the form of a time and dose log. Indeed, detecting when out-dosing is actually performed is a very good indication of the administration of a dose of drug. The display may show the actual dose being set by a user using the button 512, the last dose (e.g. amounts of units expelled) and the time since last dose (or the actual time for the last dose), or the user may use the keys 516 to scroll through the log to display previous expelling data. The pen is adapted to transmit data to another system or device, which in the present context would be the cap device 10 of FIG. 1. The pen may be provided with electronic means for detecting the type of drug in a loaded cartridge, e.g. by means of RFID or an optical reader, which information may be used in calculations or generations of warnings, e.g. in case an incorrect type of insulin is loaded into a device.

Figure 8:
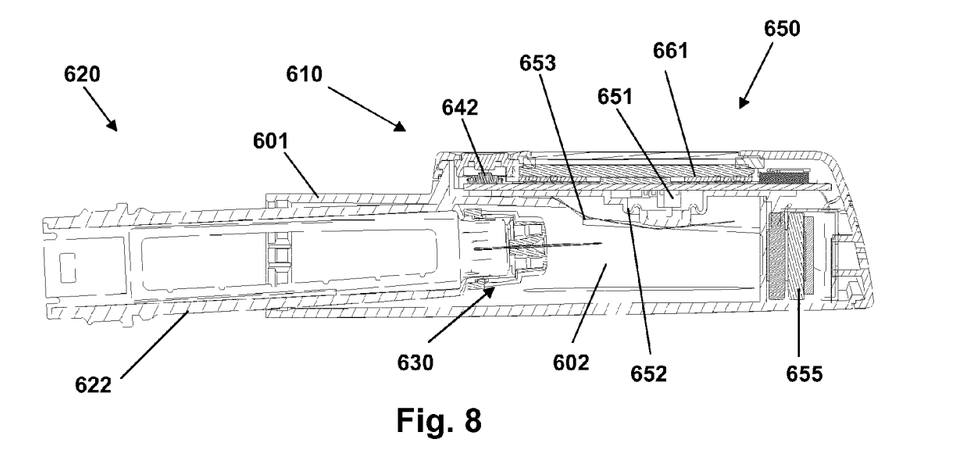
FIGS. 8-10 show a further cap device being mounted on a drug delivery device.
Figure 9:
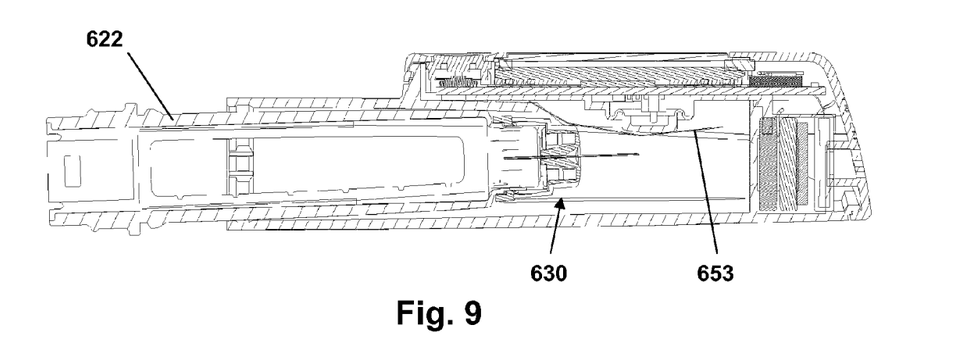
Figure 10:
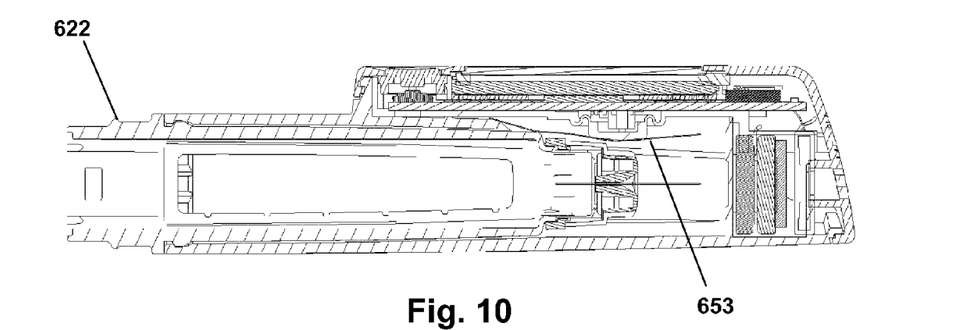

With reference to FIG. 5 a cap comprising switch means adapted to be actuated by axial movement when the cap is mounted on the distal end of a corresponding drug delivery device. With reference to FIGS. 8-10 an alternative design is disclosed in which mounting of a cap onto (or de-mounting from) a corresponding drug delivery device is detected by radial movement of a switch.

More specifically, FIG. 8 shows a cap device 610 (which in the shown embodiment does not comprise a BGM) adapted to receive a distal part 620 of a drug delivery device. The cap device comprises a housing 601 with a receiving cavity 602 having an oblong configuration defining a general axis and in which a cartridge holder 622 with a mounted needle assembly 630 can be inserted in a first direction. The cap further comprises contact means adapted to engage the cartridge holder when inserted into the receiving cavity, the contact means being actuatable between an initial position and an actuated position, wherein the contact means is moved in a radial direction relative to the first direction when moved between the initial and actuated position. The contact means comprises a moveable contact surface adapted to engage the cartridge holder when received in the receiving cavity, the contact surface being inclined relative to the general axis, this allowing an axial force exerted by the second member on the contact surface to move the contact surface in a radial direction to thereby actuate electronic switch means.

More specifically, the cap device is provided with electronic circuitry comprising switch 651, an energy source 655, controller, memory and transmission means 650, button contacts 642 and a display 661. The switch 651 is covered with a flexible elastomeric gasket 652 on which a leaf spring 653 acts, the leaf spring comprising the inclined contact surface facing towards the cavity opening. The leaf spring has a proximal end attached to the housing as well as a free distal end, this allowing the spring to easily flex radially and thus activate the switch via the gasket.

In FIGS. 8-10 insertion of a drug delivery device in the cap device 610 is shown. In the shown embodiment a needle assembly 630 is mounted on the distal end of the cartridge holder, this providing that the leaf spring initially is deflected radially by the needle assembly, however, without a needle assembly mounted the leaf spring would be deflected by the needle mount portion of the cartridge holder. Further, as can be seen in FIG. 10, in the fully mounted position the leaf spring is hold in its fully radially deflected position by the cartridge holders distal shoulder portion.

The display shown in the above-described embodiments is quite small. Whether the device contains a rechargeable battery, a replaceable battery or a non-replaceable battery, there is a need for a battery indicator in order to show the remaining capacity of the battery. Normally the indicator is shown in all screen views, however, if the display is small a relatively large part of the total area is reserved for the battery indicator at the expense of the primary information on the display.

Figure 11:
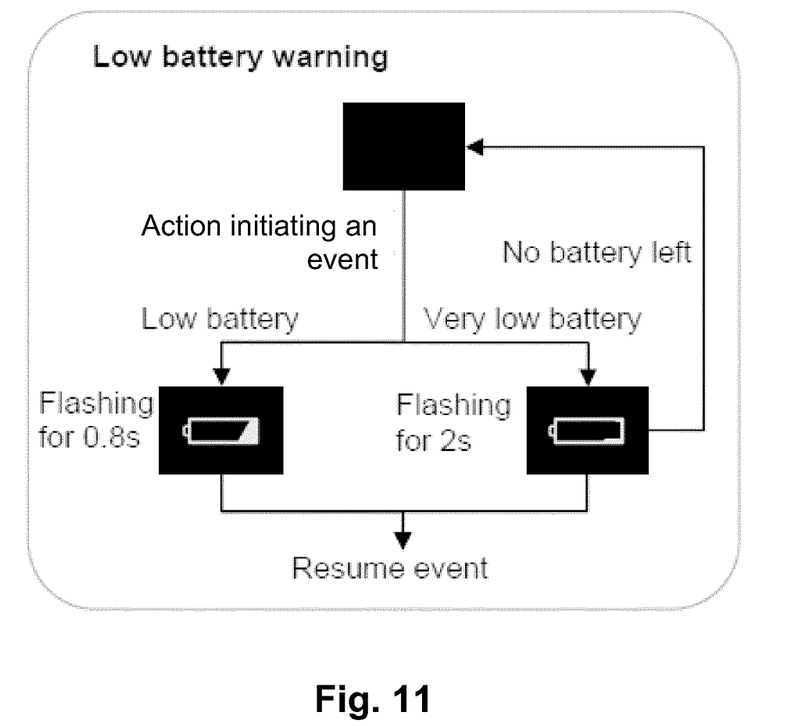
FIG. 11 shows a flow-chart for a display low-battery warning.

Correspondingly, FIG. 11 shows schematically an embodiment of a display which is controlled in an adaptable way to show only relevant information to thereby fully utilize a small display area. When the battery is fully charged or has "enough" capacity left is there no indication of the battery status. When the battery is discharged to a certain low level of remaining capacity is a low battery warning shown as the first thing for a short period when the user activates the device before continuing with the intended action. When the battery is discharged to a critical level of remaining capacity, an empty battery warning is shown as the first thing for a longer period when the user activates the device before continuing with the intended action. When the battery is almost fully discharged an empty battery warning is shown before the device returns to idle mode. In the shown example the display is a graphical display of the dot matrix type, however, the feature could also be implemented using a simple 7-segment display. For example, an "88" display may show "bt" (for "battery"), or an "8888" display may show "bAtt".

Thus, the user only has to think about recharging the device when it is necessary and the entire area of a small display can be used for the at any time most relevant information.

In the above description of the preferred embodiment, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A system for optimizing a patient's basal insulin dosage regimen over time, comprising:
   a blood glucose meter for receiving a patient blood sample and generating a blood glucose data set corresponding to a blood glucose value of the patient blood sample,
   detecting means that detect when a patient-actuated operation is performed, the operation being indicative of an administration of a dose of an insulin containing drug,
   memory means that to store:
   blood glucose data sets corresponding to a plurality of blood glucose values as a function of time,
   data representing detected patient-actuated operations as a function of time, and data representing an initial basal insulin dosage regimen,
   a processor operatively connected to the memory means, the processor being programmed to determine, based on blood glucose data sets determined at a plurality of times, whether and by how much to vary a component in a present insulin dosage regimen in order to maintain future blood-glucose-level measurements within a pre-defined range, and
   output means that communicate to the patient a component in the patient's insulin dosage regimen,
   wherein the processor is programmed to disregard a given blood glucose data set if no patient-actuated operation has been detected in a pre-defined amount of time prior to generating the given data set.

2. The system of claim 1, comprising a drug delivery assembly, the drug delivery assembly comprising:
   a drug delivery device comprising:
   a reservoir for a drug,
   an outlet for the drug,
   a drug expelling mechanism for expelling drug from the reservoir and out through the outlet, and
   a cap device releasably mountable on the drug delivery device and adapted to cover the outlet in a mounted position, the cap device comprising:
   the blood glucose meter,
   the memory means and the processor,
   the output means, and
   the detecting means,
   wherein the detection means is adapted to detect a cap-off event when the cap has been at least partially de-mounted from the drug delivery device for a pre-determined amount of time, a cap-off event being indicative of the administration of a dose of an insulin containing drug.

3. The system of claim 1, comprising a drug delivery assembly, the drug delivery assembly comprising:
   a drug delivery device comprising:
   a reservoir for a drug,
   an outlet for the drug,
   a drug expelling mechanism which can be set to expel a desired dose of drug from the reservoir and out through the outlet when actuated, and
   means that detect, store, and transmit dose data representing the size of an expelled dose, the expelling being indicative of the administration of a dose of an insulin containing drug, and
   a cap device releasably mountable on the drug delivery device and adapted to cover the outlet in a mounted position, the cap device comprising:
   the blood glucose meter,
   the memory means and the processor,
   the output means, and
   the detecting means,
   wherein the detection means is adapted to receive dose data from the drug delivery device.

4. The system of claim 1, comprising a drug delivery assembly, the drug delivery assembly comprising:
   a drug delivery device comprising:
   a reservoir for a drug,
   an outlet for the drug,
   a drug expelling mechanism for expelling drug from the reservoir and out through the outlet,
   the blood glucose meter,
   the memory means and the processor,
   the output means, and
   the detecting means,
   wherein the detection means that the detecting means adapted to detect when the drug expelling mechanism has been actuated, the expelling being indicative of the administration of a dose of an insulin containing drug, and
   a cap device releasably mountable on the drug delivery device and adapted to cover the outlet in a mounted position.

5. The system of claim 1, wherein a given blood glucose data set is disregarded by the processor if the given blood glucose data set corresponds to a blood glucose value outside a predefined range.

6. A method for optimizing a patient's basal insulin dosage regimen over time, comprising:
   determining a blood glucose value a plurality of times over time,
   detecting when a patient-actuated operation is performed, the operation being indicative of the administration of a dose of an insulin containing drug, and
   determining, based on determined blood glucose values, whether and by how much to vary a component in a present insulin dosage regimen in order to maintain future blood-glucose-level measurements within a pre-defined range,
   wherein a given blood glucose value is disregarded if no patient-actuated operation has been detected in a pre-defined amount of time prior to generating the given blood glucose value.

7. The method of claim 6, further providing an assembly comprising:
   a blood glucose meter,
   a drug delivery device, and
   a processor configured to determine, based on the determined blood glucose values, whether and by how much to vary a component in a patient's insulin dosage regimen in order to maintain the patient's future blood-glucose-level measurements within a predefined range.

8. The method of claim 7, wherein the patient-actuated operation is expelling of a dose of drug from the drug delivery device.

9. The method of claim 7, wherein the drug delivery device comprises a main part with a drug expelling mechanism and a cap adapted to be releasable mountable on the main part, the patient-actuated operation being an at least partial de-mounting of the cap from the drug delivery device for a pre-determined amount of time.

10. The method of claim 9, wherein the blood glucose meter is arranged in the cap.

* * * * *

UNITED STATES PATENT AND TRADEMARK OFFICE
CERTIFICATE OF CORRECTION

| | |
|---|---|
| PATENT NO. | : 9,636,461 B2 |
| APPLICATION NO. | : 14/115799 |
| DATED | : May 2, 2017 |
| INVENTOR(S) | : Henrik Bengtsson et al. |

Page 1 of 1

It is certified that error appears in the above-identified patent and that said Letters Patent is hereby corrected as shown below:

In the Claims

Column 11, Line 21, Claim 1, please correct the claim to read:
"…memory means that store…"

Signed and Sealed this
Seventh Day of November, 2017

Joseph Matal
*Performing the Functions and Duties of the*
*Under Secretary of Commerce for Intellectual Property and*
*Director of the United States Patent and Trademark Office*